(12) United States Patent
Fujinuma et al.

(10) Patent No.: US 8,025,702 B2
(45) Date of Patent: Sep. 27, 2011

(54) TWO-PART HAIRDYE COMPOSITION

(75) Inventors: Hiroyuki Fujinuma, Tokyo (JP);
Takashi Matsuo, Tokyo (JP); Masahiko Ogawa, Tokyo (JP); Hajime Miyabe, Tokyo (JP); Kazuhiro Okada, Tokyo (JP); Tomohito Koshika, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/739,091

(22) PCT Filed: Oct. 24, 2007

(86) PCT No.: PCT/JP2007/001161
§ 371 (c)(1),
(2), (4) Date: Apr. 21, 2010

(87) PCT Pub. No.: WO2009/054028
PCT Pub. Date: Apr. 30, 2009

(65) Prior Publication Data
US 2010/0299848 A1    Dec. 2, 2010

(51) Int. Cl.
*A61Q 5/10* (2006.01)
(52) U.S. Cl. .................. 8/405; 8/431; 8/457; 8/526
(58) Field of Classification Search .............. 8/405, 431, 8/457, 526
See application file for complete search history.

(56) References Cited

U.S. PATENT DOCUMENTS

| 2004/0213752 A1* | 10/2004 | Fujinuma et al. ........... 424/70.1 |
| 2010/0126522 A1 | 5/2010 | Fujinuma et al. |
| 2010/0126523 A1 | 5/2010 | Fujinuma et al. |
| 2010/0316583 A1 | 12/2010 | Fujinuma et al. |

FOREIGN PATENT DOCUMENTS

| JP | 9 136818 | 5/1997 |
| JP | 11 139945 | 5/1999 |
| JP | 11-199454 | 7/1999 |
| JP | 2003 119113 | 4/2003 |
| JP | 2004-262854 A | 9/2004 |
| JP | 2004-323390 A | 11/2004 |
| JP | 2004 339216 | 12/2004 |
| JP | 2005-162665 A | 6/2005 |
| JP | 2005-330193 A | 12/2005 |
| JP | 2006 124279 | 5/2006 |
| JP | 2007 291016 | 11/2007 |
| WO | WO 2010/103795 | 9/2010 |

(Continued)

OTHER PUBLICATIONS

U.S. Appl. No. 12/769,182, filed Apr. 28, 2010, Fujinuma, et al.

(Continued)

*Primary Examiner* — Eisa B Elhilo
(74) *Attorney, Agent, or Firm* — Oblon, Spivak, McClelland, Maier & Neustadt, L.L.P.

(57) ABSTRACT

Provided is a two-part hair dye composition, including a first part containing an alkali agent, a second part containing hydrogen peroxide, and a non-aerosol type foamer container for discharging a mixture solution of the first part and the second part as foam, in which the mixture solution contains the following components (A) and (B): (A) 0.1 to 10% by mass of a nonionic surfactant, and (B) 0.1 to 5% by mass of a cationic surfactant, and the mass ratio of the component (A) to the component (B) (content of the component (A)/content of the component (B)) is 1 to 100.

5 Claims, 2 Drawing Sheets

FOREIGN PATENT DOCUMENTS

WO    WO 2010/103796    9/2010

OTHER PUBLICATIONS

U.S. Appl. No. 12/739,835, filed Apr. 26, 2010, Fujinuma, et al.
U.S. Appl. No. 12/739,610, filed Apr. 23, 2010, Fujinuma, et al.
U.S. Appl. No. 12/739,631, filed Apr. 23, 2010, Miyabe.
U.S. Appl. No. 12/739,471, filed Apr. 23, 2010, Miyabe, et al.
Office Action issued Oct. 20, 2009, in Japanese Patent Application No. 2006-121136.
U.S. Appl. No. 12/995,388, filed Nov. 30, 2010, Ogawa, et al.
Notice of Reasons for Rejection mailed May 10, 2011 in Japanese Patent Application No. 2006-121136 filed Apr. 25, 2006 (w/English Translation).

* cited by examiner

Fig. 1

Fig. 2 ic hair dye composition which is easily applied to the head hair and has a high conditioning effect while maintaining features of the Patent Document 1.
TWO-PART HAIRDYE COMPOSITION

TECHNICAL FIELD

The present invention relates to a two-part hair dye composition.

BACKGROUND ART

While liquid or creamy hair dye compositions have been widely used so far, it is difficult to apply these compositions to the head hair evenly. In particular, in the case of consumers themselves applying a hair dye composition to their own head hair at the roots or on the back of the head, they need to acquire skills of "blocking" or using two mirrors facing each other ("two-mirror technique"), or the like, and a careful operation is required to apply the composition evenly.

Accordingly, discharging a composition as foam in order to simplify the hair dyeing operation has been proposed, and hair dyes of a two-part aerosol type and those of a one-part non-aerosol type, for example, are known. However, those of a two-part aerosol type have some problems: for example, uneven bleaching or uneven dyeing is likely to occur due to an inconsistent mixing ratio of a first part and a second part, a pressure-proof metal container or the like is oxidized and corroded by hydrogen peroxide, and the internal pressure of the pressure-tight container is excessively increased by degradation of hydrogen peroxide. Furthermore, since such a one-part non-aerosol type has no or weak bleaching ability, it is difficult to achieve a great change in the color tone by one time procedure. Therefore, a problem arises, i.e., a hair dyeing operation tends to be cumbersome since a hair dye is required to be left to develop for a long time and the procedure is required to be repeated after application.

On the other hand, discharging a two-part hair dye composition as foam from a non-aerosol type foamer container (e.g., Patent Documents 1 and 2) has been proposed. By discharging a mixture solution of a first part and a second part from a foamer container as foam, variation in the mixing ratio hardly occurs compared to conventional two-part aerosol hair dyes and a sufficient bleaching or hair dyeing ability may be obtained compared to conventional one-part non-aerosol hair dyes.

[Patent Document 1] JP-A-2004-339216
[Patent Document 2] JP-A-2006-124279

SUMMARY OF THE INVENTION

The present invention provides a two-part hair dye composition, including a first part containing an alkali agent, a second part containing hydrogen peroxide, and a non-aerosol type foamer container for discharging a mixture solution of the first part and the second part as foam, wherein the mixture solution contains the following components (A) and (B):
(A) 0.1 to 10% by mass of a nonionic surfactant, and
(B) 0.1 to 5% by mass of a cationic surfactant,
and a mass ratio of the component (A) to the component (B) (a content of the component (A)/a content of the component (B)) is 1 to 100.

Further, the present invention provides a head hair dyeing method, including:
discharging the mixture solution of the two-part hair dye composition described above as foam from a non-aerosol type foamer container; applying the foam to a head hair; and then re-foaming on the head hair.

DESCRIPTION OF SYMBOLS 1 respective components of two-part hair dye composition
2 first container
3 second container
4 body of squeeze container
5 squeeze foamer
6 squeeze container
A1 first part
A2 second part
A3 mixture solution

DETAILED DESCRIPTION OF THE INVENTION

The present invention relates to a foam type two-part hair dye composition which is easily applied to the head hair and has a high conditioning effect while maintaining features of the Patent Document 1.

The inventors of the present invention have found that the above-mentioned object can be achieved by incorporating a nonionic surfactant and a cationic surfactant at a given proportion into a mixture solution of the first part and the second part of the two-part non-aerosol type hair dye composition.

According to the present invention, the mixture solution of the two-part hair dye composition is discharged as foam, can be applied evenly and simply to the head hair, and exhibits a high conditioning effect. Further, the foam of the discharged mixture solution causes no liquid dripping after the application to the head hair. In addition, the foam does not cause irritation to the scalp and spattering of the agent, and has sufficient bleaching or dyeing performance. Therefore, the two-part hair dye composition of the present invention can achieve a uniform and more even bleaching finish or hair dyeing finish in a simple and comfort manner.

Further, the mixture solution discharged as foam by gas-liquid mixing using a non-aerosol type foamer container easily reaches the roots of the head hair, and the mixture solution spreads throughout the head hair to form an appropriate thin layer without forming liquid accumulation or the like at the site. Thus, the root portions do not become extremely bright, and there are no uneven bleaching and uneven dyeing due to the uneven adhesion amount of the mixture solution as frequently seen in cases of using conventional compositions such as a liquid or cream form. Accordingly, through application of the two-part hair dye composition of the present invention to the head hair in the vicinity of newly growing areas such as the parting and face line, any color difference between newly growing areas and already dyed areas may also be avoided to provide a natural finish. Further, because the mixture solution may be applied to the head hair in an appropriate amount, damages to the head hair may be reduced.

DEFINITION

In the present invention, the head hair refers to the hair grown on the head, and the concept thereof does not include the hair separate from the head such as a wig and a tress.

Furthermore, the head hair may be the hair of a doll or any animal, but human head hair is preferred.

The two-part hair dye composition as used herein is a concept that includes both of a hair dye composition containing a dye and a bleach composition containing no dye. The head hair dyeing method is a concept that includes a head hair bleaching method.

[Alkali Agent]

Examples of the alkali agent contained in the first part include ammonia, alkanolamine such as ethanolamine, sodium hydroxide, and potassium hydroxide. Furthermore, ammonium salt such as ammonium hydrogen carbonate and ammonium chloride, carbonate such as potassium carbonate and sodium hydrogen carbonate, and the like may be suitably added as buffer.

pH of the mixture solution of the first part and the second part in the two-part hair dye composition of the present invention is preferably 8 to 11, more preferably 9 to 11, and the amount of the alkali agent used is suitably adjusted so that the mixture solution should have the above-mentioned pH.

[Hydrogen Peroxide]

The content of hydrogen peroxide in the second part is preferably 1 to 9% by mass, more preferably 3 to 6% by mass. The content of hydrogen peroxide in the mixture solution of the first part and the second part is preferably 1 to 6% by mass, more preferably 2 to 5% by mass. Further, the pH of the second part is preferably 2 to 6, more preferably pH 2.5 to 4, to prevent degradation of hydrogen peroxide.

[(A): Nonionic Surfactant]

Examples of the nonionic surfactant of the component (A) include polyoxyalkylene alkyl ether, polyoxyalkylene alkenyl ether, polyoxyalkylene fatty acid ester, alkylglyceryl ether, polyglycerine fatty acid ester, fatty acid alkanol amide, sugar ether type, sugar ester type, and sugar amide type. Preferred examples thereof include alkylpolyglycoside, polyoxyalkylene alkyl ether and alkylglyceryl ethers. Alkyl polyglycoside preferably include an alkyl group having 8 to 18 carbon atoms, more preferably 8 to 14, even more preferably 9 to 11, and this alkyl group is preferably linear. The average degree of polymerization of a glucoside is preferably 1 to 5, more preferably 1 to 2. Polyoxyalkylene alkyl ether is preferably an ether having an alkyl group having 10 to 22 carbon atoms, more preferably 12 to 18, and this alkyl group is preferably linear. Furthermore, polyoxyethylene alkyl ethers are more preferred, and of these, the average addition mole number of oxyethylene group is 1 to 40, more preferably 4 to 30. Alkylglyceryl ethers preferably include an alkyl group having 8 to 18 carbon atoms, more preferably 8 to 12, and this alkyl group is preferably branched.

The component (A) may be used in a combination of two or more thereof, and the content thereof in the mixture solution of the first part and the second part is 0.1 to 10% by mass, preferably 0.5 to 7% by mass, and more preferably 1 to 5% by mass.

[(B): Cationic Surfactant]

The cationic surfactant which may be used as a component (B) is one used for a hair rinse and a softening agent, and for example, one represented by the following general formula (1).

[wherein $R^1$, $R^2$, $R^3$ and $R^4$ independently represent a hydrocarbon group which may have a substituent; at least one of $R^1$ and $R^2$ has 8 to 36 carbon atoms, and the rest thereof have 1 to 7 carbon atoms, or both of $R^3$ and $R^4$, together with the nitrogen atom to which they are attached, may form a 5- to 7-membered ring containing one ring nitrogen atom and optionally containing further ring heteroatoms selected from the group consisting of nitrogen atom, oxygen atom and sulfur atom, and said ring being optionally substituted with alkyl groups having 1 to 4 carbon atoms. $A^-$ represents an anion.]

Here, examples of the hydrocarbon group include a linear or branched alkyl group, a linear or branched alkenyl group, an aryl group and an aralkyl group, and examples of the substituent include a hydroxy group, an alkoxy group, an aryloxy group, an epoxy group, an amino group, a mono- or dialkyl amino group, a trialkyl ammonium group, a fatty acid amide group, and a fatty acid ester group. In addition, examples of the ring formed by $R^3$ and $R^4$ together with the adjacent nitrogen atom include a morpholine ring, an imidazoline ring, a piperazine ring, a piperidine ring and a pyrrolidine ring.

Examples of the anion include a chloride ion, a bromide ion, an iodide ion, a methyl sulfate ion, an ethyl sulfate ion, an acetate ion, a phosphate ion, a sulfate ion, a lactate ion, and a saccharin ion.

Specific examples of the component (B) include cetyl trimethyl ammonium chloride, stearyl trimethyl ammonium chloride, isostearyl trimethyl ammonium chloride, lauryl trimethyl ammonium chloride, behenyl trimethyl ammonium chloride, octadecyl trimethyl ammonium chloride, cocoyl trimethyl ammonium chloride, cetyl trimethyl ammonium bromide, stearyl trimethyl ammonium bromide, lauryl trimethyl ammonium bromide, isostearyl lauryl dimethyl ammonium chloride, dicetyl dimethyl ammonium chloride, distearyl dimethyl ammonium chloride, dicocoyl dimethyl ammonium chloride, γ-gluconamidopropyl dimethyl hydroxyethyl ammonium chloride, di(polyoxyethylene(2)) oleyl methyl ammonium chloride, dodecyl dimethyl ethyl ammonium chloride, octyl dihydroxyethyl methyl ammonium chloride, tri(polyoxyethylene(5)) stearyl ammonium chloride, polyoxypropylene methyl diethyl ammonium chloride, lauryl dimethyl(ethylbenzyl) ammonium chloride, behenamidopropyl-N,N-dimethyl-N-(2,3-dihydroxypropyl) ammonium chloride, tallow dimethylammoniopropyl trimethyl ammonium dichloride, and benzalkonium chloride.

The component (B) is preferably a monoalkyl trimethyl ammonium salt or a dialkyl dimethyl ammonium salt, i.e. wherein $R^1$, or $R^1$ and $R^2$, represent (s) preferably a linear or branched alkyl group having 8 to 30, more preferably 10 to 24, even more preferably 12 to 18 carbon atoms, and the rest thereof is a methyl group. Of those, a monoalkyl trimethyl ammonium salt is preferred.

The component (B) may also be used in a combination of two or more thereof, and the content thereof in the mixture solution of the first part and the second part is 0.1 to 5% by mass, preferably 0.2 to 3% by mass, and more preferably 0.3 to 1% by mass.

Further, in order to provide fine foaming property and a high conditioning effect, the mass ratio of the component (A) to the component (B) (content of the component (A)/content of the component (B)) in the mixture solution is 1 to 100, preferably 2 to 75, more preferably 3 to 50, and even more preferably 5 to 25.

When the two-part hair dye composition of the present invention is used for dyeing the head hair, the first part contains an oxidation dye or a direct dye. As a surfactant that is incorporated in the first part in order to dissolve these dyes, a nonionic surfactant of the component (A) is preferred to be mainly used, in view of the high ionic strength of the first part due to ammonia or carbonate contained in the first part.

[(C): Higher Alcohol]

In order to improve foam-holding property and to enhance an effect of suppressing liquid dripping during being left to stand after the application to the head hair, the two-part hair dye composition of the present invention may further contain, as a component (C), a higher alcohol. Higher alcohols preferably include an alkyl or alkenyl group having 10 to 30 carbon atoms, more preferably 12 to 24 carbon atoms, even more preferably 14 to 22. Of these, those including an alkyl group, more preferably a linear alkyl group are preferred. Examples of the higher alcohol as component (C) include myristyl alcohol, cetyl alcohol, stearyl alcohol, behenyl alcohol, isostearyl alcohol, and oleyl alcohol. Two or more thereof may be used in combination.

The component (C) may also be used in a combination of two or more thereof, and may be incorporated into any one of or both of the first part and the second part. The content of the component (C) in the mixture solution of the first part and the second part is preferably 0.01 to 0.8% by mass, more preferably 0.1 to 0.7% by mass, and even more preferably 0.2 to 0.6% by mass from viewpoints that foaming property is not inhibited at a low solution temperature, and that the effect of preventing dripping during the foam being left to develop is improved.

[(D): Dimethyl Diallyl Ammonium Chloride-Acrylamide Copolymer]

In order to improve an effect of preventing liquid dripping, the two-part hair dye composition of the present invention may further contain, as a component (D), a dimethyl diallyl ammonium chloride-acrylamide copolymer (INCI name: Polyquaternium-7). For example, commercially available products such as Merquat 550 (Nalco Company) may be used as the component (D).

The content of the component (D) in the mixture solution of the first part and the second part is preferably 0.01 to 3% by mass, more preferably 0.1 to 1% by mass, and even more preferably 0.2 to 0.5% by mass in order to achieve satisfactory foaming which allows easiness of application to the head hair even when the liquid temperature is low or is close to normal temperature, as well as to provide an effect for preventing liquid dripping during a period from the time of application of the mixture solution to the time of washing away thereof from the hair.

[(E): Dimethyl Diallyl Ammonium Chloride-Acrylic Acid Copolymer]

In order to control antifoaming property after the application to the hair, maintain appropriate foam duration, and facilitate the confirmation of an applied portion, the two-part hair dye composition of the present invention may further contain, as a component (E), a dimethyl diallyl ammonium chloride-acrylic acid copolymer (INCI name: Polyquaternium-22). For example, commercially available products such as Merquat 280 and Merquat 295 (manufactured by Nalco Company) may be used as the component (E).

The content of the component (E) in the mixture solution of the first part and the second part is preferably 0.01 to 0.5% by mass, and more preferably 0.1 to 0.2% by mass so that the foamability would not be inhibited at low liquid temperature and the above-mentioned effect would be obtained.

[(F): Nonvolatile Hydrophilic Solvent]

Furthermore, it is preferable to add a nonvolatile hydrophilic solvent to the first part or the second part. Consequently, irritation on the scalp may be reduced which occurs because water is evaporated from the two-part hair dye composition while leaving to develop after application of the two-part hair dye composition to the head hair, and therefore irritating components such as hydrogen peroxide are concentrated. Preferred examples of the nonvolatile hydrophilic solvent include substances without a defoaming action such as polyols and lower alkyl ethers (having 1 to 4 carbon atoms) derived therefrom. Polyols having 2 to 6 carbon atoms are preferred, and examples thereof include glycerin, diglycerin, propylene glycol, dipropylene glycol, 1,3-butanediol, ethylene glycol, diethylene glycol, isoprene glycol, and sorbitol. Examples of lower alkyl ether derived from polyol include mono-lower alkyl ethers and poly-lower alkyl ethers derived from the above-mentioned polyols (e.g., di-lower alkyl ether). Of these, mono-methyl ether and mono-ethyl ether derived from polyols are preferred, and specific examples thereof include ethylene glycol mono-methyl ether, ethylene glycol mono-ethyl ether, diethylene glycol mono-methyl ether, and diethylene glycol mono-ethyl ether. Two or more thereof may be used in combination.

The content of the nonvolatile hydrophilic solvent in the mixture solution of the first part and the second part is preferably 0.01 to 5% by mass, more preferably 0.1 to 4% by mass, and even more preferably 0.2 to 3% by mass, from viewpoints that irritation of the scalp is reduced, and that favorable foam quality is maintained even at a low solution temperature.

[Dye]

The two-part hair dye composition of the present invention may be used for bleaching of the head hair when a dye is not contained in the mixture solution of the first part and the second part, and also may be used for hair dyeing by containing an oxidative dye or a direct dye. When the composition is used for hair dyeing, the first part contains an oxidative dye or a direct dye. Examples of the oxidative dye include dye precursors such as p-phenylenediamine, toluene-2,5-diamine, o-chloro-p-phenylenediamine, N-phenyl-p-phenylenediamine, N,N-bis(hydroxyethyl)-p-phenylenediamine, 3-methyl-4-aminophenol, 2-hydroxyethyl-p-phenylenediamine, p-aminophenol, p-methylaminophenol, 4-amino-m-cresol, o-aminophenol, 1-hydroxyethyl-4,5-diaminopyrazole, and salts thereof; and couplers such as resorcin, 2-methylresorcin, 1-naphthol, 1,5-dihydroxynaphthalene, 5-amino-o-cresol, m-phenylenediamine, m-aminophenol, 2,4-diaminophenoxyethanol, 2,6-diaminopyridine, 2-methyl-5-hydroxyethylaminophenol, 2-amino-3-hydroxypyridine, and salts thereof.

Examples of the direct dye include basic dyes, nitro dyes, dispersive dyes, and cationic dyes. More specific examples thereof include 2-nitro-p-phenylenediamine, 2-amino-6-chloro-4-nitrophenol, 3-nitro-p-hydroxyethylaminophenol, 4-nitro-o-phenylenediamine, 4-amino-3-nitrophenol, 4-hydroxypropylamino-3-nitrophenol, HC Blue 2, HC Orange 1, HC Red 1, HC Yellow 2, HC Yellow 4, HC Yellow 5, HC Red 3, N,N-bis(2-hydroxyethyl)-2-nitro-p-phenylenediamine, Disperse Violet 1, Disperse Blue 1, Disperse Black 9, Basic Blue 99, Basic Brown 16, Basic Brown 17, Basic Red 76, Basic Yellow 76, Basic Orange 31, and Basic Red 51.

[Silicones]

The mixture solution of the first part and the second part of the two-part hair dye composition of the present invention is preferably free of silicones, from the standpoint that a discharged foam is maintained for a long period of time. However, silicone may be added to a certain extent to work the foam into the head hair smoothly and exert a high conditioning effect on the head hair. Examples of the silicones include dimethylpolysiloxane, methylphenylpolysiloxane, polyether-modified silicone, amino-modified silicone, and oxazoline-modified silicone elastomer, and emulsion obtained by dispersing these silicones in water using surfactants. Of these, polyether-modified silicone, amino-modified silicone, and emulsion thereof are preferred, from a viewpoint that a stable dispersion in water is enabled without using a thickening agent.

The polyether-modified silicone includes terminal-modified or side chain-modified silicones, for example, pendant type (comb type) silicones, silicones of which both terminals are modified, and silicones of which one terminal is modified. Examples of the above-mentioned modified silicone include a dimethylsiloxane-methyl(polyoxyethylene)siloxane copolymer, a dimethylsiloxane-methyl(polyoxypropylene) siloxane copolymer, and a dimethylsiloxane-methyl(polyoxyethylene-polyoxypropylene) siloxane copolymer. The polyether-modified silicone preferably has an HLB of 10 or more, and more preferably has an HLB of 10 to 18 in terms of compatibility with water. Herein, the HLB is a value determined by a cloud number (cloud number: an index having a correlation with an HLB, the index being applied to ether type nonionic surfactants).

An amino-modified silicone having an amino group or an ammonium group may be used as the amino-modified silicone, and an amodimethicone is preferred.

When silicones are used for the above-described purpose, the content of the silicones in the mixture solution of the first part and the second part is preferably 0.01 to 0.5% by mass, more preferably 0.02 to 0.4% by mass, even more preferably 0.05 to 0.3% by mass.

[Other Components]

In addition, depending on the purposes, fragrance, ultraviolet absorber, metal sequestering agent such as EDTA, disinfectant, preservative such as methyl paraoxybenzoate, stabilizer such as fenasetin, etidronic acid, and oxyquinoline sulfate, organic solvent such as ethanol, benzyl alcohol, and benzyloxyethanol, water-soluble polymer such as polyquaternium-6, polyquaternium-39, and hydroxyethylcellulose, moisturizing agent and the like may be added to the first part and the second part. Furthermore, using water as the main medium in the mixture solution of the first part and second part is preferable.

It should be noted that a persulfate salt such as ammonium persulfate may be incorporated as a third part into the mixture solution in order to further enhance a bleaching effect.

[Viscosity]

The viscosity of the first part (25° C.) is preferably 1 to 50 mPa·s, more preferably 3 to 40 mPa·s, even more preferably 5 to 30 mPa·s. The viscosity of the second part (25° C.) is preferably 1 to 300 mPa·s, more preferably 3 to 200 mPa·s, even more preferably 5 to 100 mPa·s. The viscosity of the mixture solution of the first part and the second part (25° C.) is 1 to 100 mPa·s, preferably 3 to 50 mPa·s, more preferably 5 to 30 mPa·s. The value of viscosity is defined as a value obtained after rotating Rotor No. 1 of Type B Rotational Viscometer (model TV-10) produced by Tokimec Inc. for 1 minute. Measurement is performed at 60 rpm for 100 mPa·s or lower, 30 rpm for 100 to 200 mPa·s, and 12 rpm for 200 to 500 mPa·s. By adjusting the viscosity of the mixture solution within the above-mentioned range, the mixture solution may be mixed uniformly without foaming and easily applied to the head hair, foam is well worked into the head hair, and uniform foam that hardly drips after application to the head hair may be obtained.

By adjusting the viscosity within the above-mentioned range, quality of foam that may be easily applied to and worked into the head hair may be provided, foam may be prevented from dripping down after application to the head hair, and foam may be easily discharged using a non-aerosol type foamer. In order to adjust viscosity to fall within the above-mentioned range, water-soluble solvents such as ethanol may be added, or contents and types of surfactant, polyols, higher alcohol, and the like may be suitably adjusted.

[Gas-Liquid Mixing Ratio]

The gas-liquid mixing ratio of air in foam discharged using a foamer container to the mixture solution is preferably 10 to 50 mL/g, more preferably 15 to 40 mL/g, even more preferably 20 to 30 mL/g, from viewpoints that the compositions may be easily applied to and worked into the head hair. It is noted that the gas-liquid mixing ratio here is a value measured as follows.

The gas-liquid mixing ratio is calculated by measuring the mass and the volume of foam discharged at 25° C. Specifically, 100 g of the mixture solution is placed in a foamer container, 20 g of foam is discharged into a 1000 mL measuring cylinder, the volume of the foam is measured at 1 minute after the start of discharge. The gas-liquid mixing ratio (mL/g) is obtained by dividing the volume (mL) of this discharged foam by 20 g, the mass thereof.

[Foamer Container]

In the present invention, the foamer container is a non-aerosol type container and is used to mix a first part and a second part or a mixture solution thereof with air and discharge them as foam without using a propellant. Use of the foamer container can also prevent the discharged compositions from spattering. In particular, a non-aerosol type container can be manufactured at low costs than an aerosol type container, the discharging rate can be easily adjusted, the container can be re-used by performing a certain treatment, and products can be handled more safely during distribution since no high-pressure gas propellant is required.

Any container may be used as the foamer container so long as it is a non-aerosol type container having a foam discharging means such as a known pump foamer container or squeeze foamer container having a foam discharging means.

The pump foamer container or the squeeze foamer container has a foam generating portion such as a net, and preferably has a thin net, from a viewpoint that, when a mixture solution of the first part and the second part is solidified to dryness causing clogging, the solids can be immediately dissolved by the flow of foam at the next discharge, resulting in resolution of clogging. In this case, the net preferably has a 50 to 280 mesh, more preferably a 90 to 250 mesh, and even more preferably a 130 to 220 mesh. Creamy foam can be produced by using a net mesh in this range. Furthermore, preferred examples of materials of such a mesh include nylon, polyethylene, polypropylene, polyester, teflon (registered trade name), carbon fiber, stainless, and so forth. Of these, nylon, polyethylene, polypropylene, and polyester are more preferred, and nylon is even more preferred.

In the foamer container used in the two-part hair dye composition of the present invention, at least one, preferably two or more of such nets are disposed. More preferably, two nets are disposed from viewpoints of economic efficiency, foam stability, and the like. In this case, a mesh through which the solution passes first is preferably as coarse as or coarser than a mesh through which the solution passes next.

In the foamer container, a portion in contact with the contents (e.g., inner wall of a container, inner wall of a foam discharging means, etc.) is preferably constituted by materials that are not corroded by alkalis or hydrogen peroxide and are able to pass oxygen generated by degradation of hydrogen peroxide.

As a product form used in the two-part hair dye composition used in the present invention containing a first part, a second part and a foamer container, the first part and the second part may be filled in respective containers separate from the foamer container, so that both the parts should be transferred to the foamer container and mixed before use. Alternatively, one part may be filled in the foamer container, and the other part may be filled in a separate container, so that the other part should be transferred into the foamer container before use. In this case, the second part is preferably filled in a foamer container composed of a container having gas permeability to prevent the increase of a pressure in the container due to oxygen generated by degradation of hydrogen peroxide, and more preferably filled in a foamer container made of a material having oxygen permeability (e.g., polypropylene or polyethylene). On the other hand, a container that hardly passes oxygen is required to be used for the first part to prevent oxidation of an oxidative dye.

[Head Hair Dyeing Method]

In order to dye the head hair with the two-part hair dye composition of the present invention, preferably, the mixture solution of the first part and the second part is discharged as foam from a non-aerosol type foamer container, the form is applied to the head hair, then the mixture solution is re-foamed on the head hair, and the foam is washed away after about 3 to 60 minutes, and preferably about 5 to 45 minutes from the application.

A two-part hair dye composition is used for hair dyeing treatment by mixing a first part and a second part immediately before use. In the present invention, the first part and the second part may be mixed by any of the following procedures:

1) Mixing before filling in the main body of a foamer container;
2) Mixing in the main body of a foamer container;
3) Mixing by joining the first part and the second part together in a gas-liquid mixing chamber of a foamer;
4) Once foaming the first part and the second part separately and then mixing by joining them together before discharging from the foamer;
5) Mixing separately discharged foams of the first part and the second part before applying to the head hair; or
6) Mixing separately discharged foams of the first part and the second part on the head hair.

Of those, from the viewpoints of allowing simplifying the structure of the foamer container, freely designing the compositions of the first part and the second part, and mixing in a reliable and uniform manner, 1) mixing is performed before being charged into the body of the foamer container, or 2) mixing is performed in the body of the foamer container, is preferred.

It is preferable to comb the head hair in advance of application of discharged foam. Consequently, the hair hardly gets tangled during the re-foaming treatment, so that the hair dye composition is not likely to splatter. Furthermore, after the head hair is combed, blocking, generally performed in application of a hair dye composition, is not required, and it is preferable not to perform blocking. Consequently, the hair dye composition is easily applied to the head hair or re-foamed as described later.

From viewpoints of even hair dyeing, prevention of dripping, and a sufficient hair dyeing effect, it is preferable that hair dressing is not applied to the head hair to which the hair dye composition is to be applied immediately before the hair dyeing. Furthermore, from viewpoints that the mixture solution is not diluted, even hair dyeing can be provided, dripping may be prevented and a sufficient hair dyeing effect may be obtained, dry head hair is preferred. When the hair is washed immediately before the hair dyeing treatment, it is preferable to dry the head hair before hair dyeing treatment. Drying the head hair means that the liquid, mainly water, attached due to the hair wash is removed at least to the extent that it does not drip in a spontaneous state. Specifically, it is preferable to dry the hair with a towel or a dryer.

The mixture solution of the first part and the second part discharged as foam is applied to the head hair after placing it on the hands or a brush, or directly. Here, when hands are used, it is preferable to wear gloves. According to the dyeing method of the present invention, since blocking generally performed in the application of a hair dye composition is not required, the foam may be applied in a short time. Therefore, the application of foam may be started at any head hair site, and it is not necessary to apply it starting with the neckline unlike conventional liquid or creamy two-part hair dye compositions. It is sufficient to start the application at a concerned portion, and it is preferable to apply foam from the hairline of the head hair or a site where the hair is parted.

It is preferable to discharge foam in about the size of a lemon because it is the proper size to place on one hand and to easily apply to the head hair using hands. In this case, foam is discharged with one hand and received with the other hand. Then, after foam received on the hand is once applied to the head hair, foam is discharged on the hand again to repeat the application to the head hair. This series of operations may be performed very conveniently in a short period.

Furthermore, foam may be applied to the whole head hair or only a specific portion.

Then, the applied foam is re-foamed on the head hair. The foam may be re-foamed by injecting a gas, using an instrument such as a vibrator or a brush, or with fingers. However, since the two-part hair dye composition may be thoroughly spread to the roots of the head hair, it is more preferable to use fingers. The rate of foaming using a vibrator or a brush or with fingers is preferably controlled so that the foam should not spatter.

Here, the timing of re-foaming may be after the foam has disappeared completely, during the process of disappearance, or before the applied foam changes. Alternatively, the timing may be after the foam has been completely applied to the area that needs applying the foam or during the process of application. Re-foaming may be performed continuously once or intermittently in several times. Here, when a vibrator, a brush, or fingers used for re-foaming remain in contact with a part of the head hair, or they are brought into contact within 1 second even if they are once separated, the re-foaming is assumed as continuous. In short, it is sufficient to observe the applied site and suitably foam at least before liquid drips from the applied foam. Irrespective of the property of the foam, dripping may be prevented by re-foaming the foam that almost disappears. Furthermore, by re-foaming, foam may be changed to the quality suitable for hair dyeing regardless of differences in the structure of the foamer container or the property of the foam depending on the composition of the two-part hair dye composition. In some cases, dripping may be prevented, and the foam quality suitable for hair dyeing may be maintained as it is by using a specific structure of the foamer container or a specific composition of the two-part hair dye composition.

Even in such cases, however, it is preferable to perform re-foaming at least once as early as possible after the completion of the foam application. By performing re-foaming at an early stage, uneven coloring in an area that needs applying may be prevented. This timing is preferably within 5 minutes after the completion of application of the discharged foam to the head hair, more preferably within 3 minutes, even more preferably within 1 minute.

Hereafter, specific examples of preferred procedures in the processes from discharge of foam to application to the head hair and re-foaming will be shown according to partial hair dyeing and whole head hair dyeing.

[Partial Hair Dyeing]

1) Discharge a suitable amount of foam on one hand, apply the foam to a part of the head hair, and perform one operation of re-foaming over 1 second to 10 minutes, preferably 3 seconds to 3 minutes.

2) Discharge a suitable amount of foam on one hand, apply the foam to a part of the head hair, perform one operation of re-foaming over 1 second to 10 minutes, preferably 3 seconds to 3 minutes, and repeat the operation 2 to 30 times. Re-foaming is performed over a total of 2 seconds to 20 minutes, preferably 5 seconds to 5 minutes.

[Whole Head Hair Dyeing]

3) Discharge a suitable amount of foam on one hand, apply the foam to a part of the head hair, and perform one operation of re-foaming over 3 seconds to 10 minutes, preferably 5 seconds to 3 minutes. Repeat this operation to apply the foam over the whole head.

4) Discharge a suitable amount of foam on one hand, apply the foam to a part of the head hair, and perform one operation of re-foaming over 3 seconds to 10 minutes, preferably 5 seconds to 3 minutes. Repeat this operation to apply the foam over the whole head, and then perform one operation of re-foaming over 3 seconds to 10 minutes, preferably 5 seconds to 3 minutes. Further, discharge a suitable amount of foam on one hand, additionally apply the foam to a part of the head hair, and perform one operation of re-foaming over the whole head over 3 seconds to 10 minutes, preferably 5 seconds to 3 minutes.

5) Discharge a suitable amount of foam on one hand, apply the foam to a part of the head hair, and perform one operation of re-foaming over 3 seconds to 10 minutes, preferably 5 seconds to 3 minutes. Repeat this operation to apply the foam over the whole head. After completion of the application to the whole head, perform one operation of re-foaming over 3 seconds to 10 minutes, preferably 5 seconds to 5 minutes.

6) Discharge a suitable amount of foam on one hand, apply the foam to a part of the head hair, and perform one operation of re-foaming over 3 seconds to 10 minutes, preferably 5 seconds to 3 minutes. Repeat this operation to apply the foam over the whole head. After completion of the application to the whole head, perform one operation of re-foaming over the whole head over 3 seconds to 10 minutes, preferably 5 seconds to 3 minutes, and repeat the operation 2 to 30 times. Re-foaming is performed over a total of 6 seconds to 20 minutes, preferably 10 seconds to 5 minutes.

7) Discharge a suitable amount of foam on a brush, and apply the foam to a part of the head hair. Repeat this operation to apply the foam over the whole head, and perform one operation of re-foaming over the whole head using the same brush over 3 seconds to 10 minutes, preferably 5 seconds to 5 minutes.

8) Discharge a suitable amount of foam on a brush, apply the foam to a part of the head hair, and perform one operation of re-foaming using the same brush or hands over 3 seconds to 10 minutes, preferably 5 seconds to 3 minutes. Repeat this operation to apply the foam over the whole head. After completion of application to the whole head, perform one operation of re-foaming using the same brush or hands over 3 seconds to 10 minutes, preferably 5 seconds to 5 minutes.

The area for re-foaming may be the whole head hair or only a specific portion. Since foam may be thoroughly spread by performing re-foaming over the whole head hair, incomplete dyeing may be prevented even if application of foam is missed at a site that may be hardly checked, such as the hair in back of the head. In partial dyeing, when re-foaming is performed on only a specific portion, the border of a dyed portion may be made unclear, and natural finishing is provided. Furthermore, when re-foaming is performed, it is very easy to visually check portions where foam has spread. Therefore, incomplete dyeing of a portion that needs dyeing may be avoided.

After completion of the foam application, the hair is washed after the foam is left for about 3 to 60 minutes, preferably about 5 to 45 minutes. In the present invention, the above-mentioned time after completion of the foam application means all the required time from completion of application of all the foam to the whole head or a desired portion to rinsing out, and is a concept including time required for re-foaming in addition to the time for simply leaving the hair. Then, the hair is suitably washed with a shampoo or treated with a conditioner, then rinsed with water, and dried.

EXAMPLES

Examples 1 to 5 and Comparative Example 1

Figure 1:
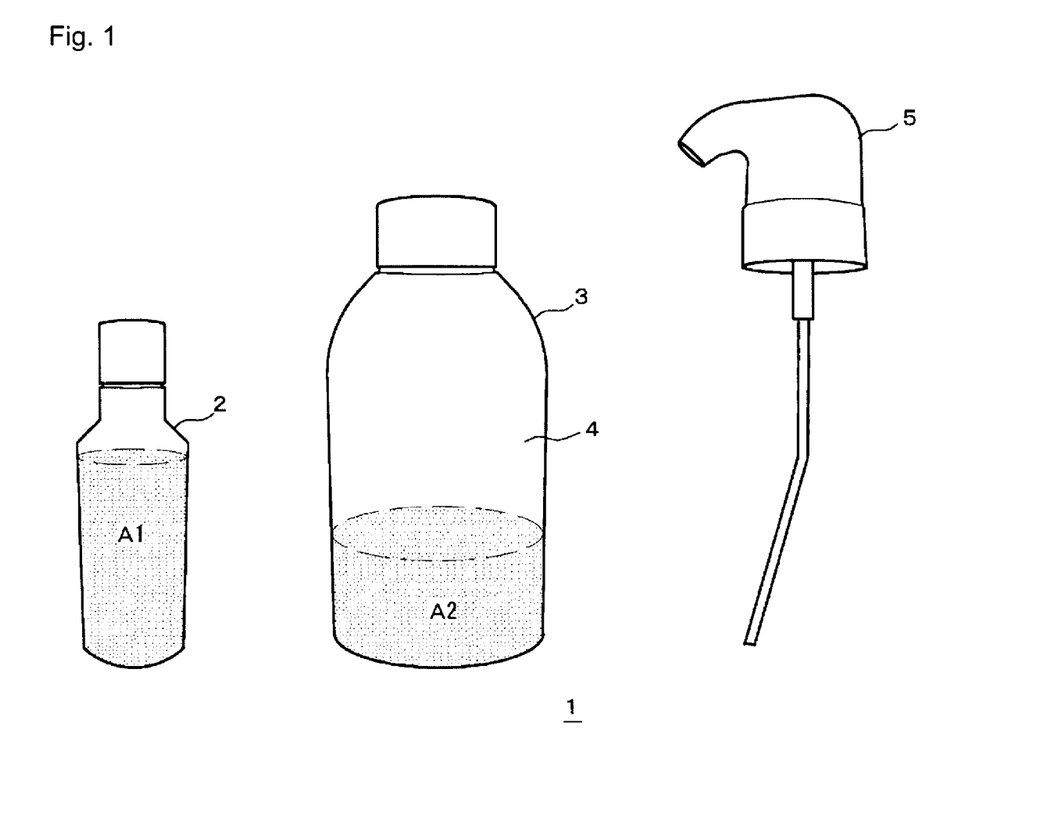
FIG. 1 shows a state of the two-part hair dye composition used in the examples and the comparative examples before mixing.

A first part and a second part having formulation (% by mass) as shown in Tables 1 and 2 were prepared. As illustrated in FIG. 1, 40 g of a first part (A1) was charged into a first container (2), and 60 g of a second part (A2) was charged into a second container (3) (also serving as container body (4) of squeeze container; internal volume: 210 mL), respectively. Further, a squeeze foamer (5) (S1 squeeze foamer manufactured by Daiwa Can Company) was prepared.

The charged first part and second part, and the squeeze foamer were given to five specialized panelists (Japanese women aged in their 20's with shoulder-length black hair) and hair dyeing was performed in accordance with the following procedure.

"Hair Dyeing Procedure"

Figure 2:
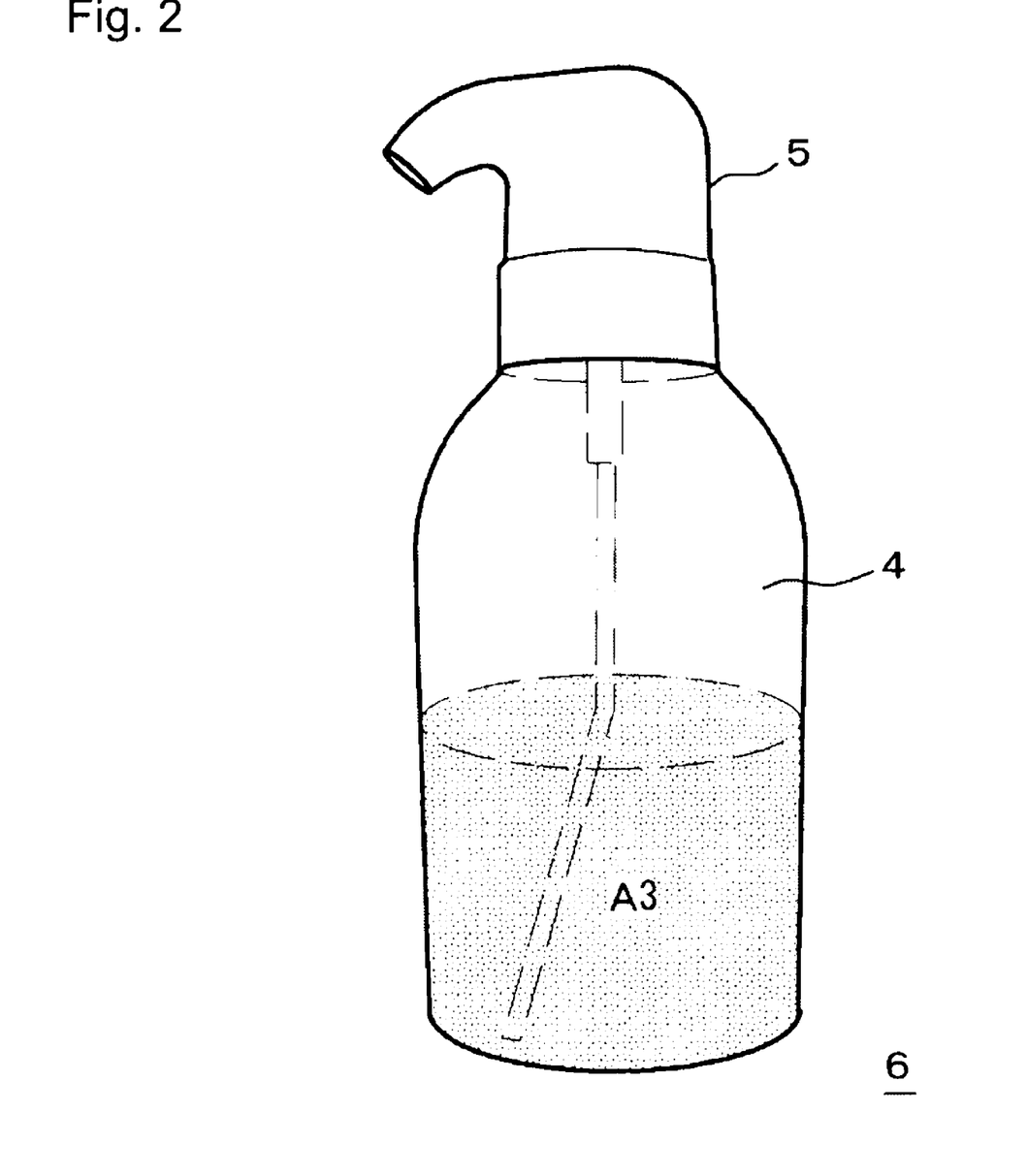
FIG. 2 shows a state of the two-part hair dye composition used in the examples and the comparative examples after mixing.

1. 40 g of a first part are charged into a container body (4) of a squeeze container charged with 60 g of a second part, the first part and the second part are mixed with each other so as not to foam a mixture solution, and then a squeeze foamer (5) is attached to the container body (FIG. 2).

2. After wearing of gloves, a squeeze container, being standing upright, is squeezed by one hand, and a foamed mixture solution is discharged in the palm of the other hand.

3. The foamed mixture solution is applied to the dried head hair.

4. By repeating the operations of the above 2 and 3, 80 g of the mixture solution are applied to the whole head hair.

5. The applied mixture solution is re-foamed by massaging of whole head hair with fingers for 15 seconds.

6. The hair is left to stand for 10 minutes.

7. The applied mixture solution is re-foamed by massaging of the whole head hair with fingers for 25 seconds.

8. After the completion of the repeated foaming operation according to the above 7, the hair is left to stand for 20 minutes.

9. The entire head hair is washed away with hot water, and shampooed, rinsed, and dried in the stated order.

With regard to "feel to the touch", "easiness of application" and "foam-holding property", a sensory evaluation was performed by the above-mentioned five specialized panelists to compare Examples 1 to 5 and Comparative Example 1. Scores were defined as described below, and the total score of the evaluation was shown in the lower columns of the formulations of Tables 1 and 2.

Example is better than Comparative Example: +2 points
Example is slightly better than Comparative Example: +1 point
Example is equivalent to Comparative Example: 0 point
Comparative Example is slightly better than Example: −1 point
Comparative Example is better than Example: −2 points

TABLE 1

| (% by mass) | Example 1 | Comparative Example 1 |
|---|---|---|
| *First part* | | |
| p-Aminophenol | 0.2 | 0.2 |
| p-Amino-o-cresol | 0.2 | 0.2 |
| Aqueous ammonia (28% by mass) | 8.0 | 8.0 |
| Ammonium hydrogen carbonate | 14.0 | 14.0 |
| Decyl glucoside | 3.2 | 3.2 |
| Laureth-23 | 2.0 | 2.0 |
| Methylparaben | 0.1 | 0.1 |
| Fragrance | 0.5 | 0.5 |
| Water | Balance | Balance |
| *Second part* | | |
| Sodium laureth sulfate | — | 1.9 |
| Stearyltrimonium chloride | 1.2 | 0.02 |
| Lauramidopropyl betaine | — | 0.05 |
| Lauryl hydroxysultaine | — | 0.05 |
| Lauric acid | — | 0.04 |
| Phosphoric acid (75% by mass) | * | * |
| Glycerin | 3.5 | 3.5 |
| Aqueous hydrogen peroxide (35% by mass) | 16.3 | 16.3 |
| Water | Balance | Balance |
| Mixing ratio of first part to second part = 1:1.5 (mass ratio) | | |
| (A) Nonionic surfactant in mixture solution (% by mass) | 2.08 | 2.08 |
| (B) Cationic surfactant in mixture solution (% by mass) | 0.72 | 0.012 |
| (A)/(B) | 2.89 | 173 |
| Evaluation Feel to the touch | 10 | — |
| Easiness of application | 2 | — |
| Foam-holding property | 2 | — |

* Amount required for adjusting second part to pH 3.8

TABLE 2

| (% by mass) | Example 2 | Example 3 | Example 4 | Example 5 |
|---|---|---|---|---|
| *First part* | | | | |
| p-Aminophenol | 0.15 | 0.15 | 0.15 | 0.15 |
| p-Amino-o-cresol | 0.2 | 0.2 | 0.2 | 0.2 |
| Toluene-2,5-diamine | 0.1 | 0.1 | 0.1 | 0.1 |
| Aqueous ammonia (28% by mass) | 6.0 | 6.0 | 6.0 | 6.0 |
| Ammonium hydrogen carbonate | 10.0 | 10.0 | 10.0 | 10.0 |
| Decyl glucoside | 11.0 | 8.0 | 6.0 | 4.0 |
| Laureth-23 | 1.0 | 1.0 | 1.0 | 1.0 |
| Propylene glycol | 4.0 | 4.0 | 4.0 | 4.0 |
| Polyquaternium-7 | 0.5 | 0.5 | 0.5 | 0.5 |
| EDTA-4Na | 0.1 | 0.1 | 0.1 | 0.1 |
| Ascorbic acid | 0.4 | 0.4 | 0.4 | 0.4 |
| Anhydrous sodium sulfite | 0.5 | 0.5 | 0.5 | 0.5 |
| Fragrance | 0.5 | 0.5 | 0.5 | 0.5 |
| Water | Balance | Balance | Balance | Balance |
| *Second part* | | | | |
| Aqueous hydrogen peroxide (35% by mass) | 16.3 | 16.3 | 16.3 | 16.3 |
| Stearyltrimonium chloride | 0.3 | 0.5 | 0.5 | 0.3 |
| Dialkyl (C12 to 18) dimonium chloride | 0.1 | — | — | 0.1 |
| Dimethicone (20 mm²/s) | 0.01 | 0.01 | 0.01 | 0.01 |
| Cetanol | 0.4 | 0.4 | 0.4 | 0.4 |
| Stearyl alcohol | 0.2 | 0.2 | 0.2 | 0.2 |
| Etidronic acid | 0.08 | 0.08 | 0.08 | 0.08 |
| Sodium hydroxide | * | * | * | * |
| Water | Balance | Balance | Balance | Balance |
| Mixing ratio of first part to second part = 1:1.5 (mass ratio) | | | | |
| (A) Nonionic surfactant in mixture solution (% by mass) | 4.8 | 3.6 | 2.8 | 2.0 |
| (B) Cationic surfactant in mixture solution (% by mass) | 0.24 | 0.3 | 0.3 | 0.24 |
| (A)/(B) | 20 | 12 | 9.33 | 8.33 |
| Evaluation Feel to the touch | 10 | 10 | 10 | 10 |
| Easiness of application | 5 | 5 | 5 | 5 |
| Foam-holding property | 8 | 7 | 7 | 8 |

* Amount for adjusting second part to pH 3.5

The invention claimed is:

1. A two-part hair dye composition, comprising a first part comprising an alkali agent, a second part comprising hydrogen peroxide, and a non-aerosol type foamer container for discharging a mixture solution of the first part and the second part as foam, wherein the mixture solution comprises the following components (A) and (B):
(A) 0.1 to 10% by mass of a nonionic surfactant, and
(B) 0.1 to 5% by mass of a cationic surfactant,
and a mass ratio of the component (A) to the component (B) (a content of the component (A)/a content of the component (B)) is 1 to 100.

2. The two-part hair dye composition according to claim 1, further comprising, as a component (C), 0.01 to 0.8% by mass of a higher alcohol in the mixture solution of the first part and the second part.

3. The two-part hair dye composition according to claim 1 or 2, further comprising, as a component (D), 0.01 to 3% by mass of a dimethyl diallyl ammonium chloride-acrylamide copolymer in the mixture solution of the first part and the second part.

4. The two-part hair dye composition according to claim 1, further comprising, as a component (F), 0.01 to 5% by mass of a nonvolatile hydrophilic solvent in the mixture solution of the first part and the second part.

5. A head hair dyeing method, comprising: discharging the mixture solution of the two-part hair dye composition according to claim 1 as foam from a non-aerosol type foamer container; applying the foam to a head hair; and then re-foaming on the head hair.

* * * * *